US006480735B2

(12) United States Patent
Colloca et al.

(10) Patent No.: US 6,480,735 B2
(45) Date of Patent: Nov. 12, 2002

(54) NEUROMUSCULAR REFLEX ASSESSMENT METHOD

(75) Inventors: Christopher J. Colloca, Phoenix, AZ (US); Tony S. Keller, Burlington, VT (US); Arlan W. Fuhr, Phoenix, AZ (US)

(73) Assignee: Activator Methods International, Ltd., Phoenix, AZ (US)

( * ) Notice: Subject to any disclaimer, the term of this patent is extended or adjusted under 35 U.S.C. 154(b) by 0 days.

(21) Appl. No.: 09/855,141

(22) Filed: May 14, 2001

(65) Prior Publication Data

US 2002/0120209 A1 Aug. 29, 2002

(Under 37 CFR 1.47)

Related U.S. Application Data

(60) Provisional application No. 60/204,462, filed on May 16, 2000.

(51) Int. Cl.$^7$ .............................................. A61B 5/0488
(52) U.S. Cl. ........................................ 600/546; 600/594
(58) Field of Search ................................ 600/546, 547, 600/587, 594, 595

(56) References Cited

U.S. PATENT DOCUMENTS

| 4,664,130 | A | * | 5/1987 | Gracovetsky | 600/546 |
| 4,971,069 | A | * | 11/1990 | Gracovetsky | 600/594 |
| 5,052,375 | A | * | 10/1991 | Stark et al. | 482/8 |
| 5,368,546 | A | * | 11/1994 | Stark et al. | 482/8 |
| 5,755,675 | A | * | 5/1998 | Sihvonen | 600/594 |
| 5,916,172 | A | * | 6/1999 | Hodges et al. | 600/546 |
| 5,929,782 | A | * | 7/1999 | Stark et al. | 128/903 |

OTHER PUBLICATIONS

"Stiffness and Neuromuscular Response of the Human Spine to Dynamic Posteroanterior Manipulative Thrust", Colloca, Keller, and Fuhr, Paper Presented at 26th Annual Meeting of the *International Society for the Study of the Lumbar Spine*, Jun. 1999.*

* cited by examiner

*Primary Examiner*—Stephen M. Hepperle
(74) *Attorney, Agent, or Firm*—Leydig, Voit & Mayer, Ltd.

(57) ABSTRACT

Studies investigating posteroanterior (PA) forces in spinal stiffness assessment have shown relationships to spinal level, body type, and lumbar extensor muscle activity. Little objective evidence is available discerning variation in PA stiffness and its clinical significance. The aim of this prospective clinical study was to determine the stiffness index and neuromuscular characteristics of the asymptomatic and symptomatic low back. Twenty-two subject underwent physical examination and completed outcome VAS, Oswestry, and SF-36 questionnaires. A hand-held spinal manipulation instrument, equipped with a load cell and accelerometer was used to deliver high rate (<0.1 sec) PA manipulative thrusts (450 N) to several common spinal landmarks including the posterior superior iliac spine (PSIS), sacral base, and L5, L4, L2, T12, T8 spinous (SP) and transverse processes (TP). Surface, linear enveloped, electromyographic (sEMG) recordings were obtained during the trusts from electrodes (8 leads) located over the L3 and L5 erector spinae. The accelerance (peak acceleration/peak force, $kg^{-1}$) or stiffness index and composite sEMG response was calculated for each of the trusts. Significantly increased SP stiffness (7.0 $kg^{-1}$) ($P<0.05$) and a more positive sEMG response was found in subjects with frequent or constant LBP symptoms in comparison to SP stiffness (6.5 $kg^{-1}$) of subjects with lesser symptom frequency. A positive sEMG response was associated with a significant increase ($P<0.05$) in the TP stiffness response to PA thrusts in comparison to negative neuromuscular responders. The average SP stiffness was 6.6% greater ($P<0.05$) and 19.1% greater ($P<<0.001$) than the average SI stiffness and average TP stiffness, respectfully.

5 Claims, 7 Drawing Sheets

NEUROMUSCULAR REFLEX ASSESSMENT METHOD

TECHNICAL FIELD OF THE INVENTION

This invention pertains to methods for assessing neuromuscular reflexes non-invasively for persons with lower back pain.

BACKGROUND OF THE INVENTION

The invention provides such a method for assessing neuromuscular reflexes through surface electromyography (EMG) simultaneously during stiffness assessments. It is a primary object of the present invention to determine the stiffness index and neuromuscular characteristics of the asymptomatic and symptomatic low back pain in subjects reporting the same. These and other advantages of the present invention, as well as additional inventive features, will be apparent from the description of the invention provided herein.

BRIEF SUMMARY OF THE INVENTION

Physical examination of patients with low back pain (LBP) has included assessment of the motion of the human spine in an attempt to assess the functional status of underlying anatomy. Clinicians have utilized mobilization palpation procedures to manually apply posteroanterior (PA) forces over various spinal segments to assess the perceived tissue resistance and pain provocation. The clinician further uses the perceived results of these assessments to formulate clinical diagnoses and to identify which spinal level to treat and supposed effectiveness of the intervention. Due to the qualitative nature of such assessments, however, many studies have demonstrated that such clinical judgments are unreliable or inaccurate (22, 39, 43, 48). For this reason, mechanical devices have been developed to more objectively quantify spine stiffness.

A series of studies have appeared investigating the reliability and validity of instruments to assess spine stiffness with favorable results. Spinal disorders may be characterized as exhibiting alterations in the mechanical behavior to loading, notably, changes in spinal stiffness. Studies investigating posteroanterior (PA) forces in spinal stiffness assessment have shown relationships to spinal level, body type, and lumbar extensor muscle activity. Such measures may be important determinants to discriminate patients with low back pain and further provide significant information of the mechanical behavior of the human spine. Little objective evidence is available however, discerning variations in PA stiffness and its clinical significance.

Although ligaments have been considered to provide primary restraint to most major joints, recently the musculature has been shown to play an important role in maintaining joint stability. Solomonow and associates reported that mechanical deformation of ligamentous tissues of the human spine could reflexively elicit activity of the paraspinal muscles providing a net effect of stiffening of the motion segment. As the spine is a complex dynamic structure whose viscoelastic makeup includes not only its discoligamentous elements, but also stabilizing musculature, we aimed to study mechanical and neuromuscular responses to dynamic PA manipulative thrusts. Specifically, the objective of this prospective clinical study was to investigate the mechanical PA stiffness of the thoracic, lumbosacral, and pelvic regions and concomitant lumbar neuromuscular responses to high loading rate PA thrusts in a group of subjects with varying degrees of LBP.

The research conducted by applicants was presented, in part, at the 26$^{th}$ Annual Meeting of the International Society for the Study of the Lumbar Spine, held in Kona, Hawaii, Jun. 21–25, 1999. A copy of applicants' full report is attached hereto and incorporated herein by reference.

The invention may best be understood with reference to the accompanying drawings and in the following detailed description of the preferred embodiments.

DETAILED DESCRIPTION OF THE INVENTION

Subjects

Twenty-two subjects (12 males & 10 females, mean age of 42.8 years SD 17.5 years, range 15–73 years) were recruited from a group of volunteers who responded to a flyer circulated in the community advertising the experiment. Subjects were included if they had not consulted a physician or therapist for low back or leg pain the past six months. Subjects were excluded if they were pregnant, had a previous history of lumbar spinal surgery, or presented any contraindication of spine stiffness testing (e.g., malignancy, inflammatory or infective processes involving the spine, significant osteoporosis, or spinal disorders including spondylolisthesis, ankylosing spondylitis, spinal fusion, or neurologic deficit). Subjects were also excluded if they complained of significant symptoms unrelated to lumbar complaints. Following written and verbal explanation of the protocol for the study, subjects signed a written informed consent form acknowledging their participation in the study.

Symptom Categorization

Subjects completed questionnaires consisting of a general health history, revised Oswestry low back disability index, and perceived health status questionnaire (SF-36). From these questionnaires, historical and demographic data was obtained to categorize low back symptomatology. Back pain history was recorded on a scale of 0–3 where 0=No LBP within the past 6 months, 1=Acute (<4 weeks of symptoms), 2=Sub-Acute (<12 weeks of symptoms), and 3=Chronic (>12 weeks of symptoms). Similarly, patients were characterized according to LBP symptom frequency within the past 6 months on a scale of 0–4 where 0=No symptoms, 1=Occasional, 2=Intermittent, 3=Frequent, and 4=Constant. The patients were also asked to provide a visual analog score (VAS), which represented their pain perception at the time of examination. The VAS score ranged from 0–10 with zero representing no pain and ten representing the worst pain imaginable.

Procedure

Figure 1:
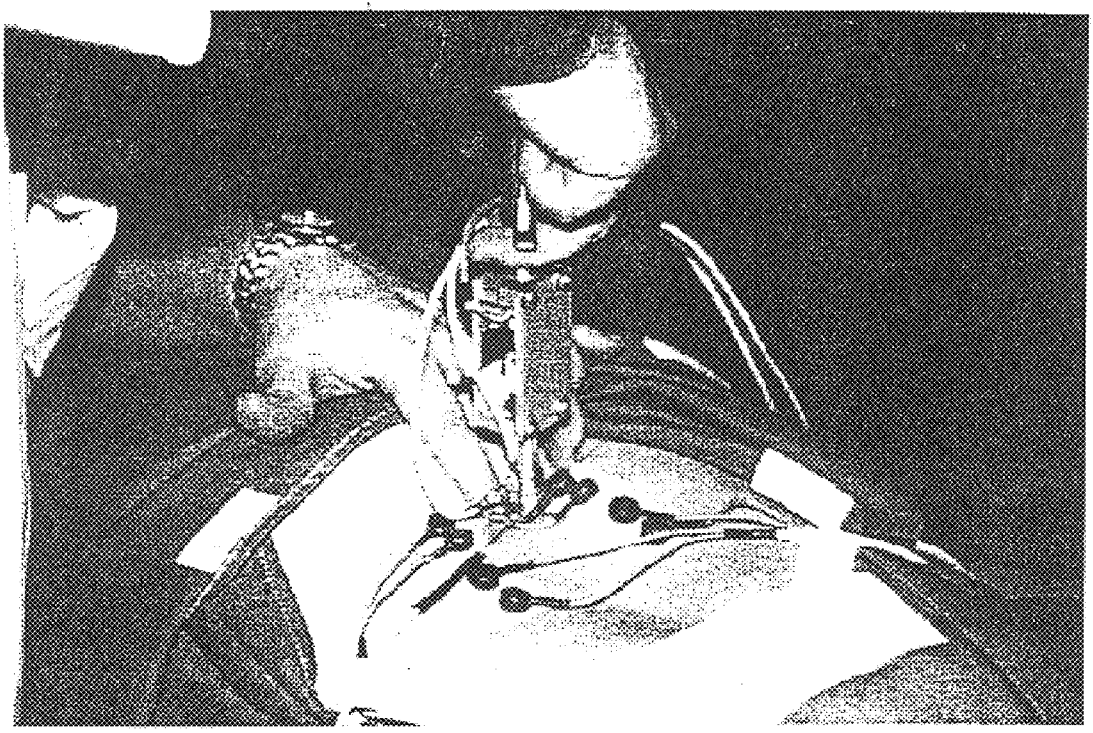
FIG. 1 is a photograph illustrating the bilateral sEMG electrode placement and Activator Adjusting Instruments used to deliver PA manipulative thrusts to the thoraco-lumbar spine and sacroiliac joints.

Following completion of the history, subjects were gowned and underwent physical examination consisting of orthopaedic and neurologic examination, lumbar range of motion, and plain film radiographic examination of the lumbar spine to rule out neurolologic deficit or spinal pathology. The review of history and physical examination was performed by a licensed chiropractic physician in accordance with standard clinical practice. Each subject was placed in the prone position by use of a motorized vertical/horizontal table (Softec/Tri-W-G, Valley City, N.Dak.). Surface, linear enveloped, electromyographic (sEMG) recordings were obtained from pre-gelled, bipolar electrodes located bilaterally over the L3 and L5 paraspinal musculature (FIG. 1). Electrode leads were spaced approximately 2 cm apart following skin preparation. Electrode pairs were positioned on the lateral aspect of the erector spinae muscle so that PA thrusts could be delivered to both the spinous processes and transverse processes.

Prior to the stiffness measurement protocol, subjects were asked to perform three consecutive maximal effort isometric trunk extensions of 5 seconds duration with a five second rest between exertions. Average peak, isometric sEMG responses obtained from the four electrode pairs were used to normalized each channel of sEMG data.

Figure 2A:
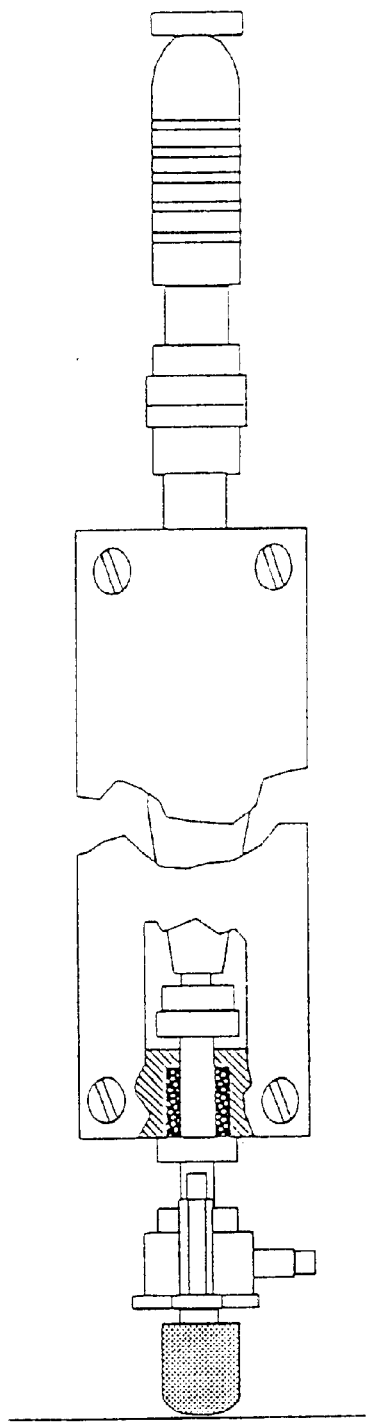
FIGS. 2a and 2b are schematic illustrations of the Activator Adjusting Instrument (AAI) used to deliver PA manipulative thrusts. An aluminum frame attached to the handle of the AAI facilitates preloading of the spine without compressing the spring actuator located in the handle of the AAI. The input load and acceleration response of the spine is measured using a dynamic load cell and accelerometer attached to the AAI stylus. The AAI delivers an approximately 450 N thrust over an time-duration of less than 10 msec.
Figure 2B:
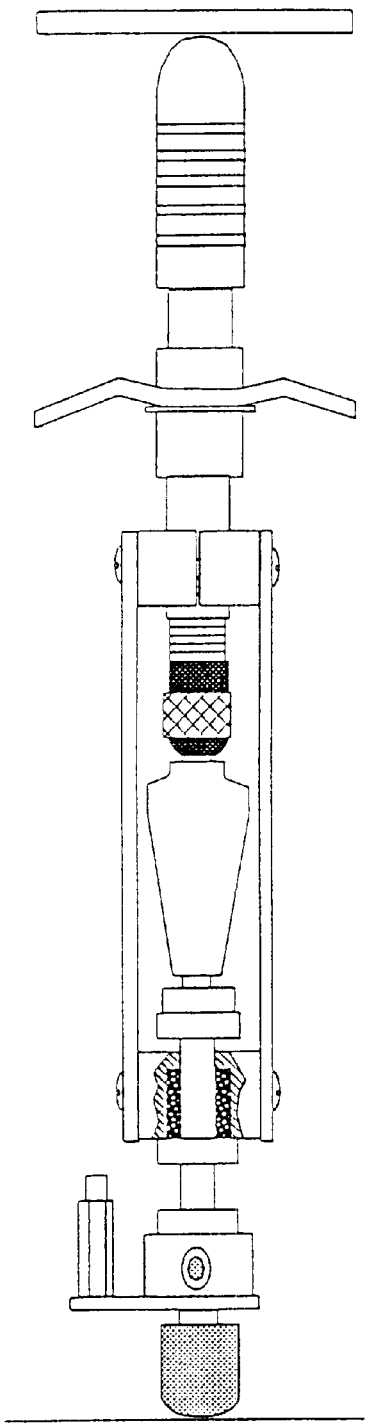
Figure 3A:
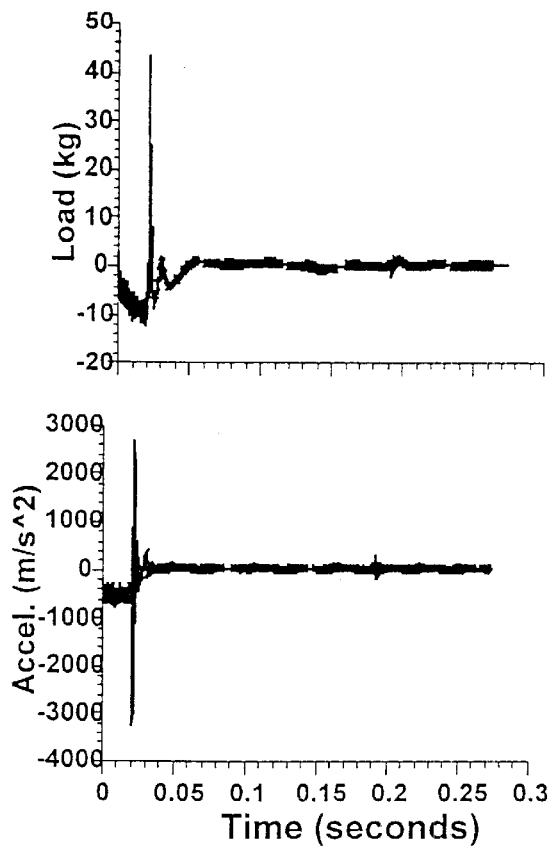
FIGS. 3a is a typical input force and acceleration response curves obtained during the application of PA manipulative thrusts to the spine (Subject 003, thrust on L4 spinous process).
Figure 3B:
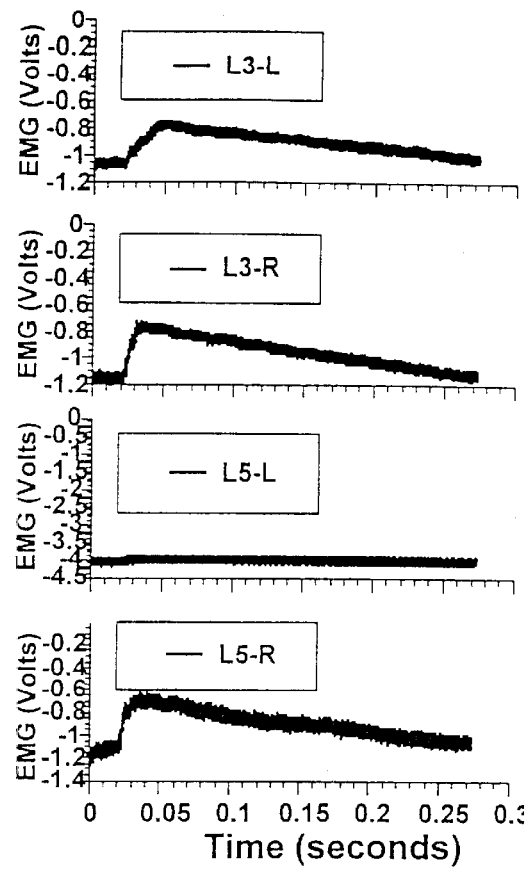
FIG. 3b shows unnormalized sEMG response for each of the four bipolar surface electrodes.

An Activator® II Adjusting Instrument (AAI II) (Activator Methods, Inc., Phoenix, Ariz.) equipped with a pre-load control frame, load cell and accelerometer was then used to deliver a PA manipulative thrust to several common spinal landmarks, including the PSIS (left and right), sacral base (left and right), S1 and L5, L4, L2, T12, T8 spinous and transverse processes (FIG. 2). The AAI II is a hand-held, manually activated, and adjustable force chiropractic instrument that produces a loading history approximately 6 msec in duration and 450 Newtons in peak amplitude (23). PA thrusts imparted to the spine were consistent with those delivered in routine clinical practice for which forces were directed perpendicular to the body surface curvature. Neuromuscular (sEMG) activity of the erector spinae muscles, load and acceleration were recorded simultaneously during each PA thrust (FIG. 3). A total of 20 PA thrusts were delivered. The accelerance (peak acceleration/peak force, $KG^{-1}$), hereafter referred to as stiffness index, was calculated for each of the thrusts.

Linear enveloped sEMG (Noraxon Myotrace 10, Finland), thrust force (PCB model 201A03, Depew, N.Y.) and acceleration (PCB model 305A04) signals were recorded using a Biopac (MP100 (Biopac Systems, Inc., Santa Barbara, Calif.) data acquisition system and Acknowledge software (Biopac Systems, Inc.). During the isometric trunk extension trials, sEMG data was collected at 50 Hz over a 30 second time interval. For the PA mechanical thrust procedure the sEMG, thrust force and acceleration responses were sampled at 10 kHz over a 273 msec time interval (see FIG. 3). An external trigger was used to initiate data collection during each of the PA thrusts. The twenty PA thrusts and 4 EMG measurements resulted in a total of 80 sEMG measurements per subject. A composite index of sEMG activity was defined to simplify characterization of this data. Namely, a positive response was defined as a sEMG response >10% of the average peak isometric extension sEMG response.

Statistical Analysis

Descriptive statistics were performed on all of the parametric data. An Analysis of Variance (ANOVA) was used to determine within group and across group differences in PA stiffness co-varying for subject age. A 2-tailed t-test was performed to assess grouped differences in functional status (FAS, Oswestry, SF-36). Statistical significance was set at a significance level of p<0.05 to test the null hypotheses that no difference in stiffness index and neuromuscular response exists between symptomatic and asymptomatic subjects.

Results

Table 1 summarizes the population, male and female patient demographics. In this study population, male subjects were significantly older than females (ANOVA, P=0.02).

TABLE 1

| Parameter | All Subjects (n = 22) | Males (n = 12) | Females (n = 10) |
|---|---|---|---|
| Age (years) | 42.8 (17.5) | 50.4 (15.1) | 33.7 (16.3) |
| Weight (kg) | 75.8 (18.0) | 86.6 (15.9) | 62.9 (10.2) |
| Height (cm) | 173.5 (10.2) | 179.3 (7.3) | 166.6 (9.1) |

Table 2 summarizes the functional status (Oswestry), symptomatology (VAS), perceived health perception (SF-36), and health history of the subjects. Approximately one-half of the subjects had a VAS score greater than 3. The mean Oswestry index was 9.7, which corresponds to a mean disability index of 19.4% for all subjects. All but one of the subjects had a perceived health status (SF-36) better than fair. In terms of symptomatology, two of the subjects were asymptomatic (no prior history of LBP), 6 had occasional LBP symptoms, 4 intermittent, and 10 had chronic symptoms of LBP. Over one-half of the subject reported that they had LBP for more than four weeks.

TABLE 2

| Parameter | Range, Score or Index | No. of Subjects | % of Subjects |
|---|---|---|---|
| VAS | 0–3 | 12 | 54.5 |
| (0–10, 10 = worst pain) | 4–7 | 10 | 45.5 |
|  | 8–10 | 0 | 0 |
| Oswestry | 0–6 | 6 | 27.3 |
| (0–50, 50 = worst score) | 7–13 | 10 | 45.5 |
|  | 14–20 | 5 | 22.7 |
|  | 21–27 | 1 | 0.05 |
| SF-36 | 0 (Excellent) | 2 | 0.1 |
|  | 1 (Very Good) | 11 | 50.0 |
|  | 2 (Good) | 8 | 36.4 |
|  | 3 (Fair) | 1 | 0.05 |
|  | 4 (Poor) | 0 | 0 |
| LBP History | ( (None) | 6 | 27.3 |
|  | 1 (Acute) | 3 | 13.7 |
|  | 2 (Sub-Acute) | 1 | 0.05 |
|  | 3 (Chronic) | 12 | 54.5 |
| LBP Symptom Frequency | 9 (None) | 2 | 9.1 |
|  | 1 (Occasional) | 6 | 27.3 |
|  | 2 (Intermittent) | 4 | 18.2 |
|  | 3 (Frequent) | 9 | 40.9 |
|  | 4 (Constant) | 1 | 4.5 |
| Positive sEMG Response | 0–7 | 6 | 27.3 |
| (0–80) | 8–15 | 8 | 36.4 |
|  | 16–23 | 2 | 9.1 |
|  | 24–31 | 4 | 18.2 |
|  | 32–39 | 2 | 9.1 |

Figure 4:
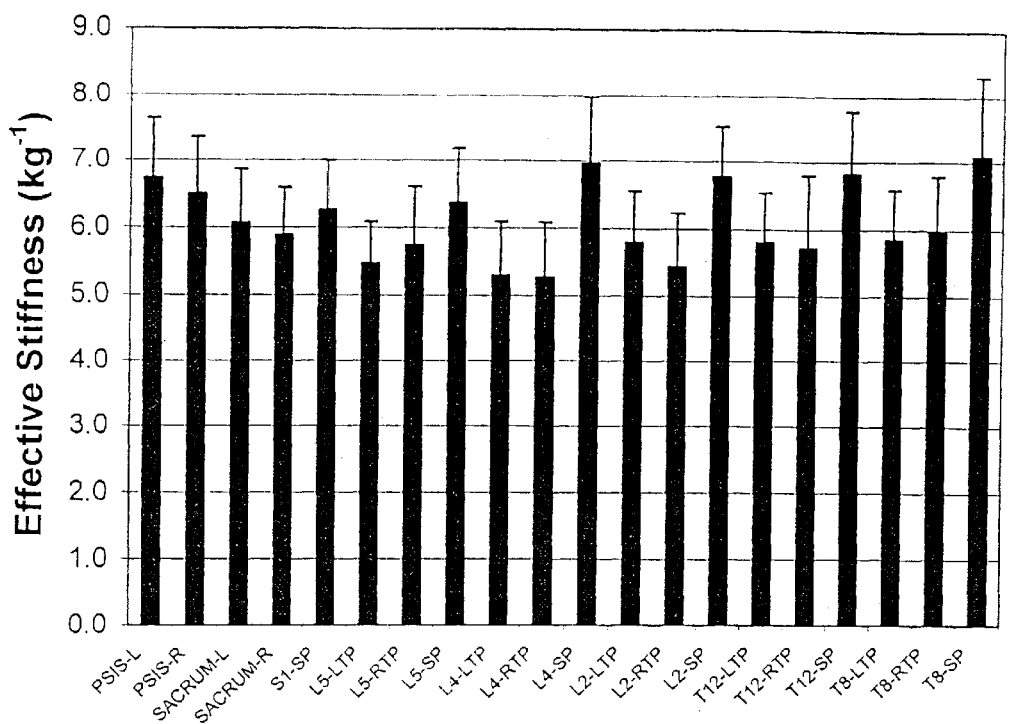
FIG. 4 is a variation in effective PA stiffness for thrusts applied to the thoraco-lumbar spinous processes (SPs) and transverse processes (TPs) and the sacroiliac region (Sacral base & Posterior Superior Iliac Spine [PSIS]). Mean values and error bars (standard deviation) are shown for each of the 20 levels examined. Differences in SP, TP and SI (PSIS+ sacrum) stiffness index were statistically significant.

Examination of FIG. 4 indicates that the PA stiffness was higher for thrusts applied over the spinous processes (SPs) in comparison to thrusts applied over the transverse processes (TPs). Thrusts applied to the sacro-iliac regio (SI=PSIS and sacrum) produced PA stiffness values in between that of the SP and TP stiffness values. Thoracic TP stiffness was significantly greater (9.9%) than the Lumbar TP stiffness (ANOVA, P<0.05). The stiffness of the Thoracic SP was not significantly different than the Lumbar SP stiffness. Differences in SI, SP, and TP stiffness were statistically significant. The average SP stiffness was 6.6% greater (ANOVA, P<0.05) and 19.1% greater (ANOVA, P<<0.001) than the average SI stiffness and average TP stiffness, respectfully. Subject mean SI, SP, and TP stiffness values were used for the group comparisons that follow.

Thrusts over the SI SP and TP regions elicited one or more positive sEMG responses in all subjects (mean composite positive sEMG response=15, range 1–33). The majority of positive sEMG responses occurred during PA thrusts applied to the lumbo-sacral spine. PA thrusts in the thoracic region elicited a positive sEMG response in only six of the 22 subjects. positive sEMG responses were observed in response to thrusts that were applied over both the spinous processes and the transverse processes. Generally, sEMG responses occurred between 2–4 milliseconds following the initiation of the PA thrust, and continued throughout the 273 msec measurement interval. In a few cases the sEMG response was initiated during the pre-load phase of the PA thrust application. The number and percentage of subject eliciting 0–7, 8–15, and so-on ranges of positive sEMG are summarized in Table 2.

Figure 5A:
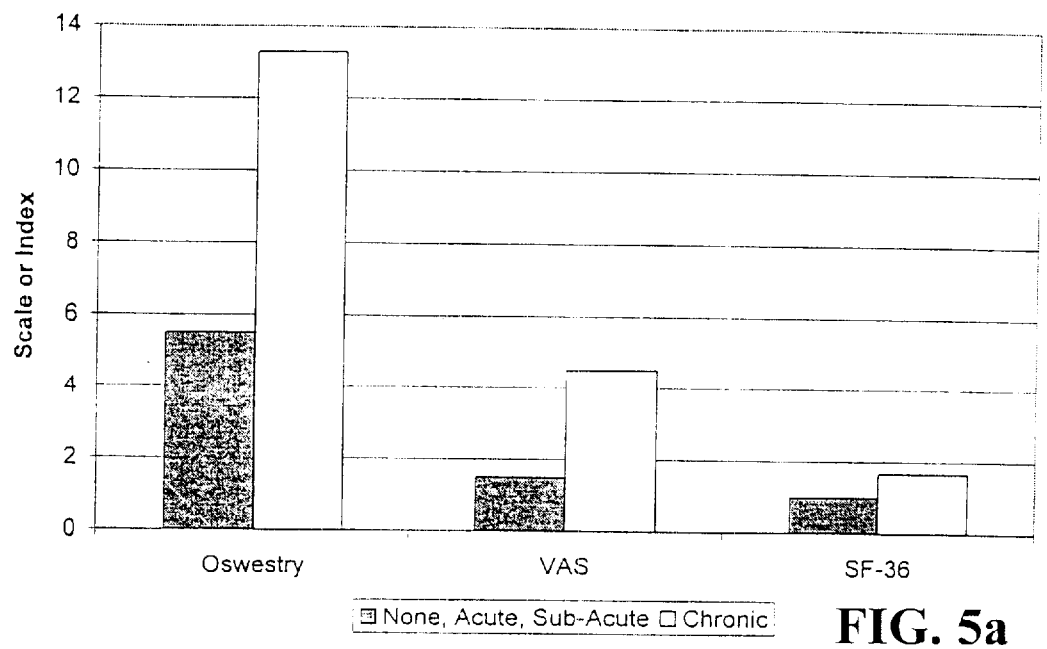
FIGS. 5a and 5b show the subjective (A) and biomechanical (B) status of the subjects grouped according to LBP chronicity. Error bars represent one standard deviation. Differences in stiffness index (SI=sacroiliac, SP=spinous process, TP=transverse process) were not significant between the chronic group and the none, acute, subacute LBP group.
Figure 5B:
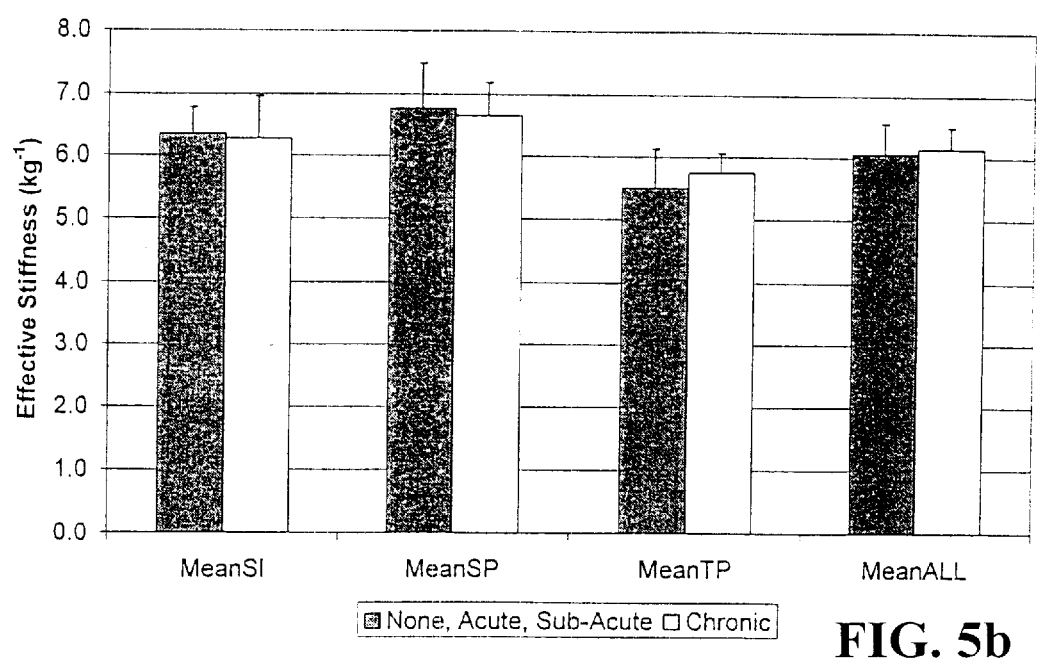
Figure 6A:
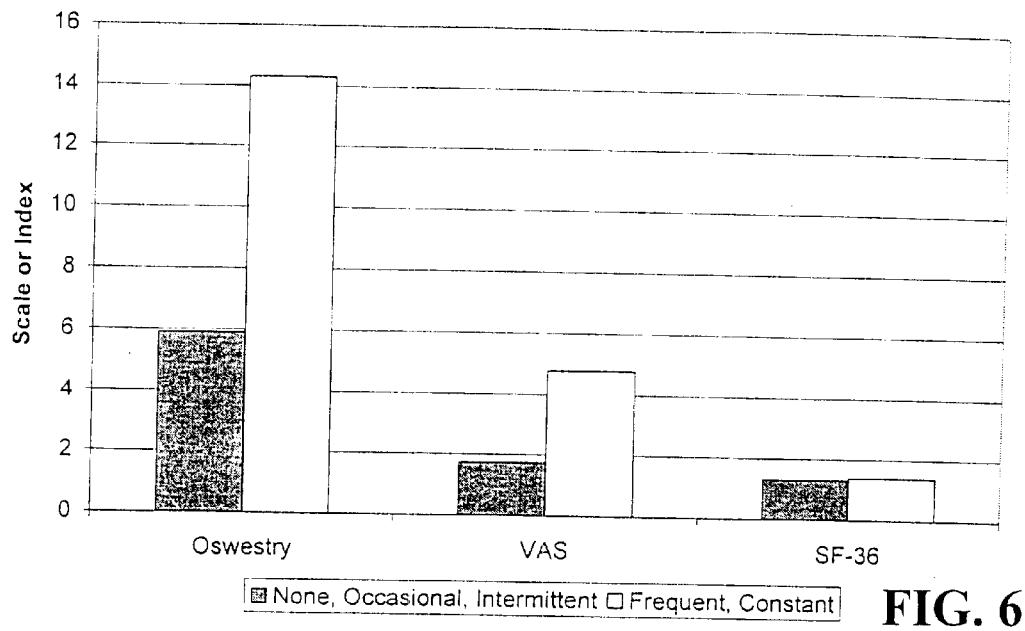
FIGS. 6a and 6b show the subjective (A) and biomechanical (B) status of the subjects grouped according to LBP symptom frequency. Error bars represent one standard deviation. Differences in stiffness index (SI=sacroiliac, SP=spinous process, TP=transverse process) were significant (SP stiffness only) between the frequency and constant LBP group and the none, occasional and intermittent LBP group.
Figure 6B:
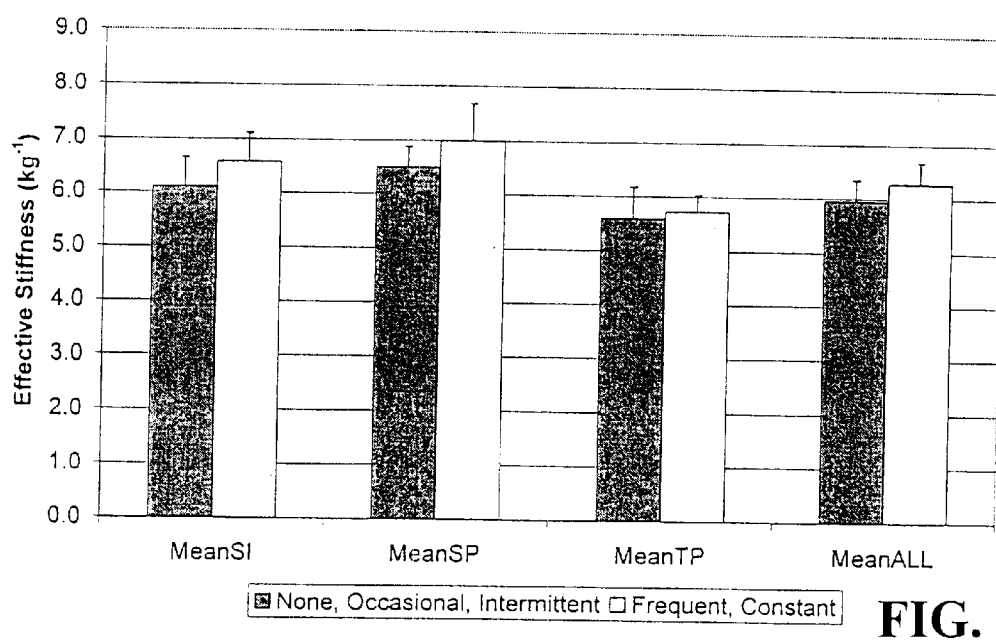

Based upon the health history findings, patients were sub-grouped according to LBP history (None, Acute or Sub-Acute vs. Chronic) and symptom frequency (None, Occasional or intermittent vs. Frequent or Constant). FIGS. 5 and 6 summarize the subjective and biomechanical status of the subjects grouped in this manner. LBP chronicity (FIG. 5a) and increased symptom frequency (FIG. 6a) were associated with a significant (t-test, P<0.001) increase in Oswestry disability index scores and VAS measures of symptom intensity, but was not associated with any significant differences in patient perception of disability (SF-36) PA stiffness (SI, SP, TP) was not significantly different (ANOVA, P>0.05) for subjects grouped according to subjects grouped according to LBP chronicity (FIG. 5b). In subjects with frequent or constant LBP symptoms, however, there was a significantly increased (ANOVA, P<0.05) SP stiffness (7.0 kg$^{-1}$) in comparison to the SP stiffness (6.5 kg$^{-1}$) of subjects with none or only occasional LBP symptoms (FIG. 6b). Patients with frequent or constant LBP symptoms also reported significantly greater VAS (t-test, P=0.001), Oswestry (t-test, P=0.001) and SF-36 perceived health status (t-test, P=0.03) scores. A more positive sEMG response was found in subjects with frequent-constant symptom frequency (mean 18/80 positive responses, range 8–33) in comparison to subjects with non-intermittent symptom frequency (12/80, range 1–27).

Figure 7A:
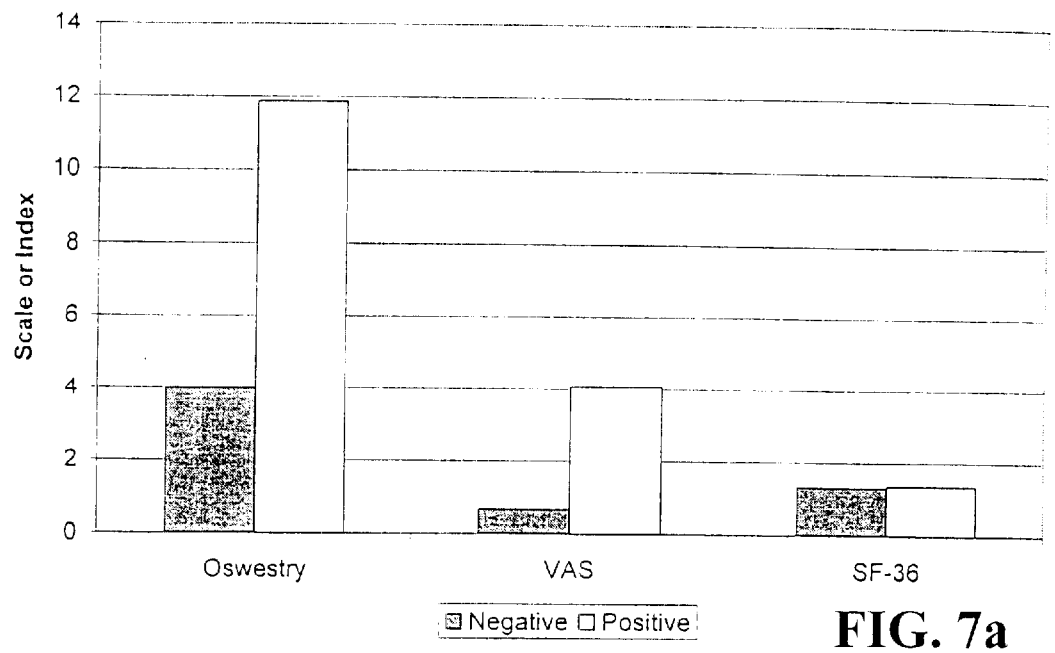
FIGS. 7a and 7b show the subjective (A) and biomechanical (B) status of the subjects grouped according the sEMG response. Error bars represent one standard deviation. Differences in stiffness index (SI=sacroiliac, SP=spinous process, TP=transverse process were significant (TP stiffness only) between the "positive" sEMG response group and the "negative" sEMG response group.
Figure 7B:
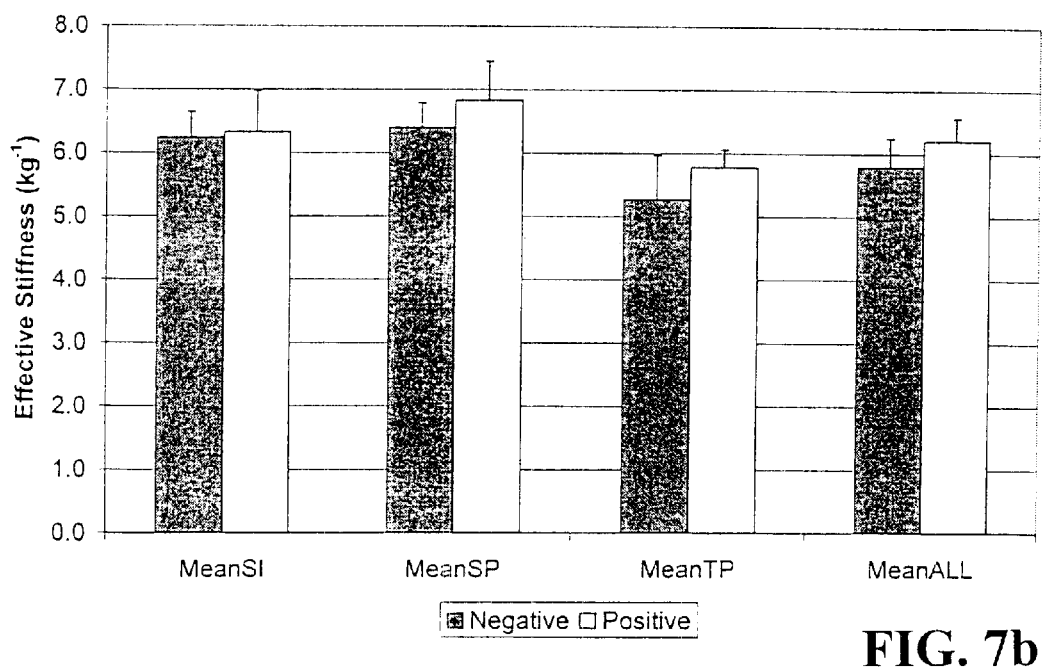

Patients were also grouped according to the number of positive sEMG responses to the PA mechanical thrusts. patients with 8 (10% of total) or more positive responses to the PA thrusts were classified as "positive" neuromuscular responders (n=16), whereas patients with fewer than 8 positive responses were classified as "negative" neuromuscular responders (n=6). Subject measures of patient status (Oswestry, VAS, SF-36) showed significant (t-test, P<0.005) group differences (FIG. 7a) that were similar to the group differences observed for LBP chronicity and symptom frequency comparisons. A "positive" sEMG response was associated with a significant increase (ANOVA, P<0.05) in the TP stiffness response to PA thrusts in comparison to "negative" neuromuscular responders (FIG. 7b). Both null hypotheses that were tested were rejected.

Discussion

Several important findings emerge from this study, most importantly additional support for clinical assessment strategies that utilize stiffness and neuromuscular measurements to probe and quantify the biomechanical characteristics of the spine. Noteworthy was the finding that "symptomatic" subjects or subjects presenting with frequent-constant LBP were characterized by having significantly increased Oswestry low back disability scores, visual analog pain scores, and SP stiffness index in comparison to more "asymptomatic" subjects or subjects presenting with none to intermittent LBP. These results are similar to those reported by Latimer and associates who demonstrated that subjects with LBP showed increased PA stiffness as compared to when they had little or no pain (26). While there was no statistically significant relationship of spinal stiffness to LBP history, the frequency of the subjects' complaints were found to be positively correlated to spinal stiffness. Thus, it may be likely that spinal stiffness is increased in subjects experiencing pain at the time of evaluation.

To our knowledge, this is the first report assessing stiffness measures applied to the skin overlying the transverse processes and sacroiliac joints. In this regard, a statistically significant decrease in stiffness index exists in TPs in both the thoracic and lumbar spine when compared to SP stiffness values. This is not surprising as there is more overlying musculature over TP bony landmarks as opposed to the SPs. Assessments made over the musculature (TPs) thus appear dampened when compared to contacts made over the SPs. The finding that thoracic TP stiffness was significantly greater (9.9%) than the Lumbar TP stiffness may be attributed to the fact that biomechanically, the thoracic spine is relatively stiffer than the lumbar spine because of the stability provided by additional spinal structures including the costal articulations and interconnecting musculature (29,33). Erector spinae muscles originating from thoracic vertebrae, have a more stable origin than muscles originating in lumbar vertebrae.

Thrusts applied to the sacroiliac region (PSIS & sacral base) produced PA stiffness values in between that of the SP and TP stiffness values. While it may be expected for more stable articulations of the SI joints to be stiffer than seen with thrusts applied over the TPs, it is curious as to why the SI were less stiff than SPs. In this regard, soft-tissue volume overlying the sacroiliac joint contacts may be an important factor as has been reported in other studies (32, 35, 50). However, to our knowledge there is no research that specifically documents to the PA stiffness of the SI joint. Considerations of body type or adiposity should be investigated in future work.

Also noteworthy was the finding that subjects with positive neuromuscular responses to PA manipulative thrusts presented with more severe disability indices, higher pain scores and increased TP stiffness in comparison to subjects with negative neuromuscular responses. Since neuromuscular responses were associated with all lumbar thrusts, but less often in response to thoracic or sacroiliac thrusts, differentiation was achieved by grouping subjects into positive and negative neuromuscular responders. Muscular responses to PA forces of ≈5–1% of subjects maximal voluntary contraction have been though to be responsible for increases in lumbar PA stiffness observed by clinicians (45). Subjects with positive neuromuscular responses may exhibit heightened muscle activity so as to stabilize the spine in response in a perceived noxious stimulus or pain. Individuals who require sustained activity of their paraspinal muscles in occupational environments are subject to muscle fatigue and diminished ability of the muscles to stabilize the spine (46). Subsequently, examination procedures geared toward understanding spinal stiffness and muscular activity may serve to identify those individuals at risk, and monitor their response to therapeutic intervention.

In the current study, generally, positive sEMG responses occurred between 2–4 milliseconds following the initiation of the PA manipulative thrust, and continued throughout the 273 msec measurement interval. As previously reported, AAI thrusts delivered to the thoracic spine of an asymptomatic subject have been associated with reflex responses in the shape of a single compound motor unit action potential (8). As similar reflex responses were observed for contacts mainly over bone (SPs) and over muscle (TPs) in our study, it is unlikely that the response simply originates from muscle spindles. The relatively long duration sEMG responses (lasting through the 273 ms of data collection) observed in our study are similar to sEMG responses that have been attributed to mechanoreceptors in the capsule of the spinal facet joints, pain and cutaneous receptors, and proprioceptors of skeletal muscles (muscle spindles and golgi tendon organs) (13). Unfortunately, as was the case with the aforementioned study cited, separation of the reflex signal into its constituent components was not possible.

Immunohistochemical neuroanatomical and neurophysiological investigation has demonstrated the existence of mechanosensitive and nociceptive afferent fibers within the discoligamentous tissues of the thoracic and lumbar spine, sacroiliac joints, and spinal musculature (1–3, 16, 38, 42, 51). Spinal ligaments not only provide mechanical stability to spinal joints, but also act as active communicators of sensory information regarding the loading or noxious presence in spinal joints (18). Through reflexogenic mechanisms, stimulation of discoligamentous structures results in reflect activity in the paraspinal musculature thereby making a contribution toward maintaining spinal stability when subjected to various internal and external disturbances (1517, 46, 47).

As observed in our study, PA manipulative thrusts applied to the thoracic spine in some cases elicited positive neuromuscular responses at sEMG leads located at the L3 and L5 spinal levels. As the erector spinae musculature consists of several muscles surpassing multiple spinal levels (20) and knowledge that sensory inputs are known to ascend or descend as much as three or four spinal levels via interneuronal connections with motor neurons (7), it is not surprising that PA thrusts cause reflex responses quite distant from the point of application. AAI thrusts applied t the T12 spinous process have been found to cause significant rotations of the L3–L4 functional spinal units which could also be responsible for such observations (40). Our finding of sEMG responses associated with all lumbar PA thrusts is consistent with the findings of Solomonow et al. who found that strongest EMG responses at the levels of electrical stimulation rather than adjacent levels (46).

Biomechanical models have shown that intersegmental agonist and antagonist muscles biomechanically increases the overall stiffness (stability) of the intervertebral joints (41). The load-bearing potential of the ligamentous spine is substantially increased by controlling its deformation modes through minimal exertion of selected muscles (24). The paraspinal musculature has been found to play a large role in maintaining spine stability (4,6). Similar conclusions have been realized by directly assessing muscular contributions to spine stiffness in a clinical setting. As reported by Lee and colleagues, PA stiffness is significantly greater during maximum activation of the lumbar extensor muscles (28). By assessing PA stiffness values during different percentages of the maximal voluntary contraction, Shirley and associates found that even small amounts of back muscle activity can increase lumbar PA stiffness (45). Muscular responses in the vicinity of ligament deformation results in increasing its resistance to mechanical disturbances to the natural alignment of the vertebrae. Our results corroborate these findings.

In another context, sEMG responses to PA manipulative thrusts as demonstrated in our study amplifies the findings of previous work. Herzog et al. (13) reported consistent neuromuscular responses to spinal manipulative treatments (SMTs) applied to different regions of the spine and pelvis in ten asymptomatic young men. Typically the SMTs delivered in this manner last approximately 200 msec (8) and are of the force magnitude ranging from approximately 100–500 N depending on the region of the spine undergoing treatment (11). These authors reported that the reflex responses occurred within 50–100 msec after the onset of the treatment thrust and lasted for approximately 100–400 msec, and were said to be composed of a series of spatially and temporally nonsynchronized motor unit action potentials of multireceptor origin. More work is required to elucidate these findings.

Moreover, as SMT has been traditionally considered to be associated with an audible joint cavitation, a series of studies have been undertaken to investigate its significance (9, 14). Slower rate SMTs (1–3 sec) were found not to produce neuromuscular reflex responses in the back musculature regardless of whether joint cavitations were elicited (8, 9, 12). Emphasis concerning the mechanical characteristics of SMTs according to this group have noted that the production of associated reflex responses depends directly on the rate of change in force and deformation during the treatment rather than on the force or stretch magnitude itself (13). The AAI II equipped with a preload control frame used in our study is a spinal manipulative device specifically designed to impart a consistent high loading rate thrust, but is not ordinarily associated with an audible joint cavitation. The AAI II has been found to impart a 450 N peak force profile over an approximately 6 msec duration, and contains a primary force peak duration of less than 0.1 msec) (23). AAI thrusts delivered to the in vivo human lumbar spine, however, produce significant displacements (axial range= 0.25–1.62 mm; PA shear range=0.1–0.51 mm), and rotations (0.13–0.9°) of functional spinal units (40). Similar motions have been reported in response to traditional SMTs (5), although subsequent to an approximate 300 N preload force (10) as opposed to a smaller preload force (60 N) used with the AAI II (40. Future work is required to elucidate the relationships between mechanical characteristics of SMTs and neuromuscular responses in an attempt to maximize potential therapeutic benefits and minimizing forces exerted to minimize potential risk to the patient.

Conclusions

The current study demonstrated increased spinal stiffness and positive neuromuscular responses in subjects with frequent-constant LBP as compared to subjects reporting none-intermittent LBP. Our findings are similar to those previously conducted using other methods. non-invasive stiffness and sEMG measurements, when combined with conservative manipulative care of the back may prove to be a particularly effective means to diagnostically probe and treat lower back disorders. As this is the first report of spinal stiffness while simultaneously monitoring neuromuscular responses, more work is necessary to better understand the relationships between mechanical and physiologic characteristics of the human spine. Measurements of PA stiffness and neuromuscular characteristics of the symptomatic and asymptomatic LBP population are particularly important for clarification of the significance of these observations.

All of the references cited or referenced herein, including patents, patent applications, and publications, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention.

We claim:

1. A method for assessing neuromuscular reflexes noninvasively for persons with lower back pain comprising the steps of:

delivering manipulative thrusts to at least one spinal landmark of a patient with a hand-held spinal manipulation instrument, obtaining electromyographic recordings during the thrusts, calculating a stiffness index and composite electromyographic response for each of the thrusts, and comparing the calculated stiffness index and electromyographic response with the same collected data from a population of subjects both symptomatic and asymptomatic of lower back pain.

2. A method according to claim 1 wherein said hand-held spinal manipulation instrument is equipped with a load cell and accelerometer to deliver high rate posteroanterior manipulative thrusts.

3. A method according to claim 2 wherein said manipulative thrusts are delivered to several common spinal landmarks.

4. A method according to claim 3 wherein the spinal landmarks include the posterior superior iliac spine, sacral base and L2, L4, L5, T8 and T12 spinous and transverse processes.

5. A method according to claim 2 wherein the rate of thrusts is .<10 msec.

\* \* \* \* \*